United States Patent [19]

Pugh, Jr. et al.

[11] Patent Number: 4,790,810
[45] Date of Patent: Dec. 13, 1988

[54] URETERAL CONNECTOR STENT

[75] Inventors: Robert W. Pugh, Jr., Lakeville; Dezso K. Levius, Bloomington, both of Minn.

[73] Assignee: American Medical Systems, Inc., Minnetonka, Minn.

[21] Appl. No.: 794,575

[22] Filed: Nov. 4, 1985

[51] Int. Cl.⁴ ............................................. A61M 25/00
[52] U.S. Cl. ....................................... 604/8; 604/283
[58] Field of Search ...................... 604/8–10, 604/54, 103, 170, 280–284

[56] References Cited

U.S. PATENT DOCUMENTS

| | | | |
|---|---|---|---|
| 2,118,631 | 5/1938 | Wappler | 128/349 |
| 3,419,010 | 11/1966 | Williamson | 128/350 |
| 3,805,794 | 4/1974 | Schlesinger | 604/103 X |
| 3,890,977 | 6/1975 | Wilson | 128/418 |
| 3,951,153 | 4/1976 | Leucci | 604/54 |
| 4,212,304 | 7/1980 | Finney | 604/170 |
| 4,307,723 | 12/1981 | Finney | 604/8 |
| 4,531,933 | 7/1985 | Norton et al. | 604/8 |
| 4,537,183 | 8/1985 | Fogarty | 128/79 |
| 4,610,657 | 9/1986 | Densow | 604/8 |

OTHER PUBLICATIONS

The New Mentor Malleable Penile Prosthesis (Brochure).
Ureteral Indwelling Double Pigtail Stent (Brochure).
Hepperlen, T. et al., Self-Retained Internal Ureteral Stents: A New Approach, J. Urol. 119 (Jun. 1978) 731–734.
Munro, R. et al., Use of Completely Implantable Urethral Catheter in Male Patients with Spinal Cord Injury., Urology 8:5 (Nov. 1976) 492–494.
Total Reliability, Mentor Corporation Brochure (reference A2) May, 1983.

Primary Examiner—Dalton L. Truluck
Attorney, Agent, or Firm—Arnold, White & Durkee

[57] ABSTRACT

A connector stent of adjustable length is provided for draining fluid through a biological passage. The connector stent comprises an elongated tubular member and a connector. A retaining means is disposed at one end of the elongated tubular member, the other end being straight. A retaining means is disposed at one end of the connector, the other end being adapted to engage the straight end of the elongated tubular member. The straight end of the elongated tubular member may be cut to a desired length before engaging the connector so that the length of the connector stent corresponds to the length of the fluid passageway to be drained.

29 Claims, 2 Drawing Sheets

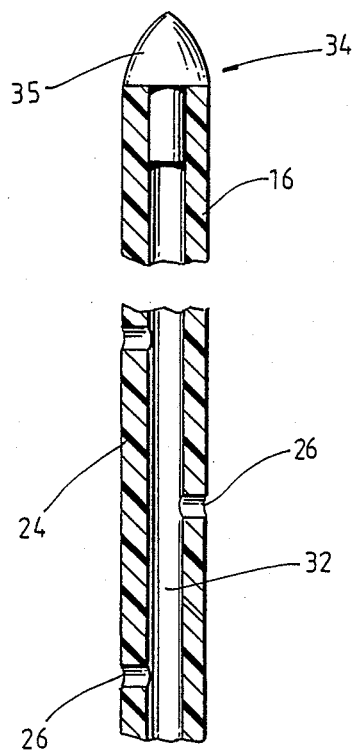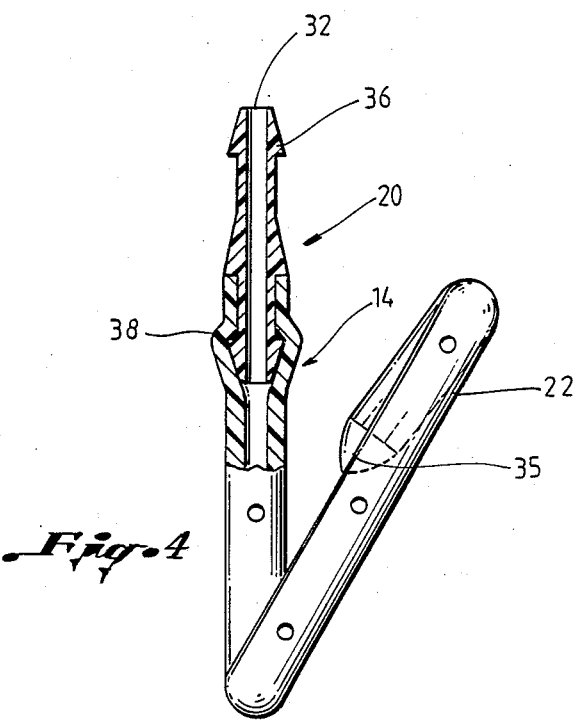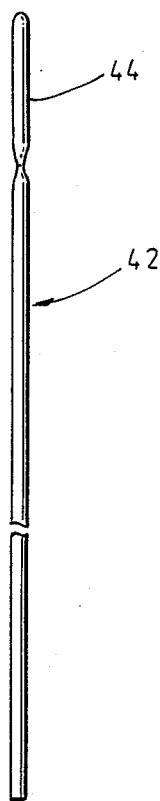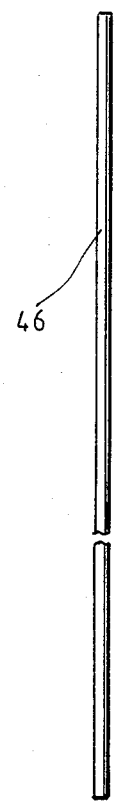

URETERAL CONNECTOR STENT

BACKGROUND OF THE INVENTION

The invention relates to catheters for continuous drainage of fluids from cavities of the body, and more particularly, to catheters of the implantable kind for the drainage of urine from the kidney and into the bladder.

Catheter stents are used to promote fluid drainage through damaged bodily passages. For example, catheter stents are used in the ureter when a cancerous growth is interfering with drainage of urine from the kidney. Also when the ureter has been damaged, for example in an auto accident, catheter stents are used to prevent leakage of urine through incisions in the urinary tract. Ureteral catheter stents are used when other types of damage have occurred in order to prevent acute angulation of the ureter during healing.

The stent is usually positioned in the desired fluid passage by insertion into and through a body orifice, incision, peripheral artery, vein, urogenital or respiratory passage. Once the need for the stent has been eliminated, however, the stent must be removed. Removal is preferably accomplished without surgery. Absent complications, ureteral catheter stents can be removed by grasping the bladder end of the stent and removing the stent through the urogenital passage. Without proper anchoring, however, a ureteral catheter stent can migrate either into the bladder or into the kidney. If the stent migrates into the kidney, surgery will be required to remove the stent. Migration not only complicates removal of the stent, but also interferes with proper fluid flow through the fluid passage being drained.

One factor which increases the possibility of migration of a stent is improper measurement of the stent in relation to the fluid passage being drained. For example, ureteral catheter stents are presently commercially available in lengths that increase by four centimeter increments for 12 to 30 centimeters. The patient having a fluid passage of a length different than these three commercially available stent lengths must bear the increased risk of stent migration or irritation. The unavailability of more varied stent lengths is not only a burden on patients, but also on hospitals. Presently, hospitals must use valuable inventory space to maintain inventory of all sizes of catheter stents.

The foregoing problems reveal the need for a catheter stent which can be more precisely measured to fit patients' needs but which helps decrease the required hospital inventory. The present invention is designed to meet these needs.

SUMMARY OF THE INVENTION

In accordance with the present invention, a catheter stent is designed so that its length may be adjusted. The ureteral connector stent of the present invention comprises an adjustable elongated tubular member and a connector.

The elongated tubular member is provided with a retaining means at one end, the other end being a straight tube. The retaining means end is preferably closed. The straight end of the elongated tubular member may be trimmed to a length corresponding to the needs of the patient and intended purpose of the stent.

The connector comprises a retaining means at one end and an adapter means at the other end. The adapter means is preferably a polysulfone fitting adapted to mate tightly within the open end of the elongated tubular member and of the connector to form a fluid connection. The connector preferably has a larger diameter than the elongated tubular member.

When the elongated tubular member has been trimmed to the desired length and connected to the connector via the adapter means, the stent is either inserted during open surgery or inserted endoscopically. To insert the stent endoscopically, a guidewire is inserted through the lumen of the stent, and the guidewire and stent are inserted into the desired fluid passage, for example, the ureter. An optional method would be to insert the guidewire into the desired fluid passage and then to push the stent onto the guidewire and push the stent into place by using a stent pusher.

The catheter stent is anchored in the fluid passage by means of the retaining means at each end. When used to drain the ureter, the retaining means of the elongated tubular member will rest within the kidney, and the retaining means of the connector will rest within the bladder. Because the connector stent will be the proper length, migration will be less likely to occur. The bladder end of the assembled stent preferably has a larger diameter than the kidney end. Any migration of the stent, because of excessive body movement or other factors, will therefore more likely be directed toward the bladder, which is the preferred direction. A stent that has migrated into the bladder can usually be removed endoscopically.

Examples of the more important features of this invention have been summarized rather broadly in order that the detailed description thereof which follows may be better understood, and in order that the contribution to the art may be better appreciated. There are, of course, additional features of the invention that will be described hereinafter and which will also form the subject of the claims appended hereto.

BRIEF DESCRIPTION OF THE DRAWINGS

FIG. 3 is an enlarged sectional view of a portion of the elongated tubular member and the closed end of the retaining means of FIG. 2.

FIG. 4 is an enlarged view of the connector of FIG. 1, in which the front portion of the adapter means has been cut away.

FIG. 5 is a guidewire used to insert the stent.

FIG. 6 is a catheter pusher used during removal of the guidewire or when pushing the stent into place along the guidewire.

DESCRIPTION OF THE PREFERRED EMBODIMENT

Apparatus

Figure 1:
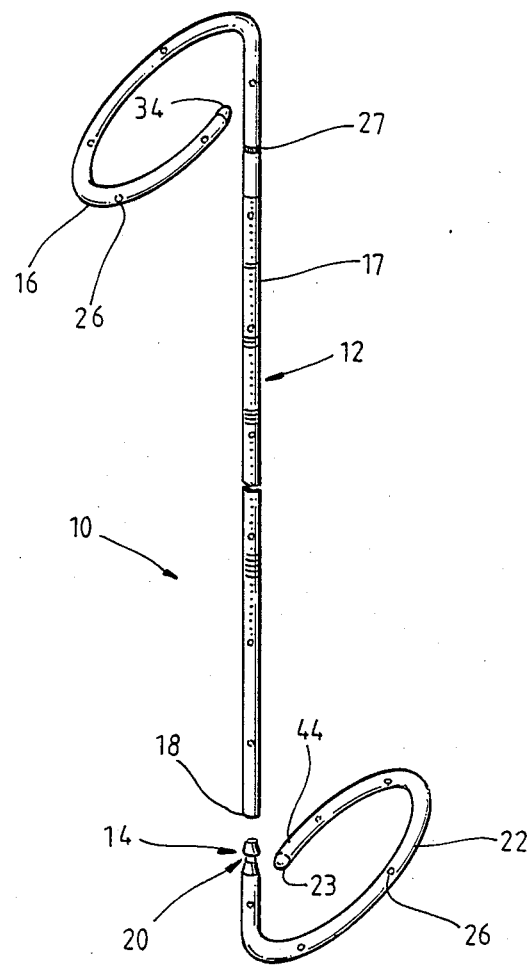
FIG. 1 is a perspective view of the ureteral connector stent prior to connecting the elongated tubular member and connector. A top and bottom view of a preferred retaining means may be seen.

Referring now to FIG. 1, the ureteral connector stent of the present invention is designated generally as 10. The stent is comprised of an elongated tubular member, designated generally as 12, and a connector, designated generally as 14. Elongated tubular member 12 has a first end comprising a retaining means 16 and a second end which is a straight tube 17. Connector 14 has an adapter means 20 at one end and a retaining means 22 at its other end.

A preferred embodiment of retaining means 16, 22 is also shown in FIG. 1 to be a gently curved spiral; however, it is to be understood that the term "retaining means" is intended to include other functionally equivalent shapes. Retaining means 16, 22 preferably have an outer diameter of approximately one inch. Retaining means 16, 22 have closed ends 34, 23, respectively.

Figure 2:
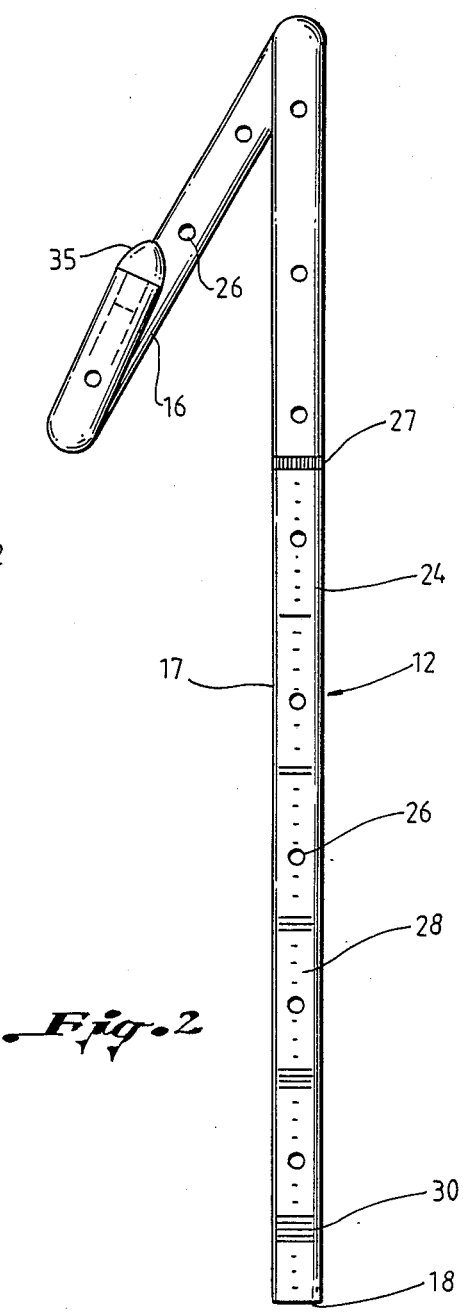
FIG. 2 is a perspective view of the elongated tubular member.

Referring now to FIG. 2, elongated tubular member 12 is illustrated in more detail. Elongated tubular member 12 is preferably composed of silicone elastomer having a durometer between 70-90, preferably 80. A suitable material is silicone homogeneously dispersed with a radiopaque material, preferably 10% barium sulfate. Elongated tubular member 12 again comprises retaining means 16 and straight tube 17. Retaining means 16 and tube 17 are formed by a wall 24 having apertures 26 therethrough and staggered 180° on one centimeter centers. Wall 24 has an average thickness-between 0.020 to 0.030 inch. Apertures 26 are preferably disposed along retaining means 16 and at least along the 30 centimeters of tube 17 adjacent to retaining means 16.

Elongated tubular member 12 may be provided in any length sufficient to allow for multiple usages of the stent. For example, elongated tubular member 12 could be used to drain the kidney to outside stoma during the immediate post operative period following urinary diversion into an isolated segment of bowel (ilium or colon). Other drainage uses would also be possible. To accommodate such multiple usages, the length of elongated tubular member 12 could range between 50-70 cm, preferably 60 cm. The listed length is the length of tube 17 not including retaining means 16. Tube 17 of elongated tubular member 12 will be trimmed to form end 18 at a point corresponding to the length of the fluid passage to be drained. Elongated tubular member 12 may be provided in various diameters,, preferably 6, 7, and 8.5 French. A radiopaque marker 27 is provided adjacent to retaining means 16. Markings 28 are provided one centimeter apart along tube 17, numbering 30 being preferably provided every five centimeters over the 30 centimeters of tube 17 adjacent to retaining means 16.

Referring now to FIG. 3, wall 24 is shown to encircle a lumen 32 through which the fluid desired to be transferred may flow. Apertures 26 permit influx of such fluid. Closed end 34 of retaining means 16 is also illustrated. End 34 is preferably closed by a plug 35.

Referring now to FIG. 4, an enlarged view of connector 14 is illustrated with the front portion of adapter means 20 being cut away. Adapter means 20 is composed of a strong, biocompatible plastic material, preferably polysulphone. Adapter means 20 is adapted to fit tightly within lumen 32 of end 18 of elongated tubular member 12 and end 38 of retaining means 22 so that the tensile strength of the resulting connection will be equal to the tensile strength of the remainder of the stent. Adhesive may be used on the connection if desired. Lumen 32 extends through adapter means 20 such that, when elongated tubular member 12 and connector 14 are connected, a continuous lumen 32 is formed.

Retaining means 22 has the same inner configuration as retaining means 16 shown in FIG. 3. If the stent is to be inserted endoscopically, plug 35 at closed end 23 of retaining means 22 may be removed by the physician in order to insert the guidewire shown in FIG. 5. Retaining means 22 is composed of the same materials as elongated tubular member 12, preferably radiopaque silicone. The outer diameter of connector 14 is preferably 2 to 3 French larger than the diameter of elongated tubular member 12.

Referring now to FIG. 5, a guidewire 42 is shown. Guidewire 42 is preferably composed of stainless steel coated with an antifriction material, preferably polytetrafluoroethylene (Teflon). The coating on guidewire 42 provides a surface to enhance the insertion of stent 10. Guidewire 42 has a diameter between 0.020 to 0.040 inch, preferably 0.038. The length of guidewire 42 can range from 120 to 180 centimeters, preferably 150 centimeters. Guidewire 42 is preferably provided with a flexible tip 44. Flexible tip 44 may be composed of stainless steel. Flexible tip 44 makes guidewire 42 easier to guide through the body into the desired fluid passage.

Referring now to FIG. 6, catheter pusher 46 is shown. Catheter pusher 46 is preferably composed of polyethylene; however, other suitable biocompatible materials may be used.

Operation

In operation, the length of the fluid passage to be drained is measured. Elongated tubular member 12 is trimmed at the desired length to form end 18. Adapter means 20 is then inserted into lumen 32 of end 18 to form a complete ureteral connector stent 10. Ureteral connector stent 10 may be inserted in this form during open surgery.

To insert ureteral connector stent 10 endoscopically, a kit including guidewire 42 and catheter pusher 46 will normally be provided. Guidewire 42 is inserted through lumen 32 of retaining means 22, adapter means 20, straight tube 17, and retaining means 16 to abut plug 35 of retaining means 16. Ureteral connector stent 10 is thereby straightened for ease of insertion into the desired fluid passageway. Guidewire 42 and stent 10 are inserted through a cystoscope into the urogenital passage. Catheter pusher 46 is inserted through the cystoscope and held against end 23 of retaining means 22 until proper placement has been achieved. Guidewire 42 is removed, and then catheter pusher 46 is removed. Catheter stent 10 will be in proper position with retaining means 16 in the kidney and retaining means 22 in the bladder. This can be verified radiographically because stent 10 is radiopaque, and on x-ray, ring 27 contrasts with stent 10 to confirm proper placement in the kidney.

When ureteral connector stent 10 is to be removed, it may be removed endoscopically on an outpatient basis using either a foreign body or biopsy foreceps or by using a stone basket.

Manufacture

To manufacture ureteral connector stent 10, raw silicone elastomer is extruded through a die to form tubing at a partially cured state, ranging from 30-50. Retaining means 16, 22 are formed by vulcanizing the tubing on curved forms. Vulcanization is completed in an oven to set the retaining means 16, 22 permanently into the silicone elastomer. The tubing is then cut to the desired length. After cutting, a mandrel is inserted through lumen 32 of the tubing and apertures 26, approximately 0.035 inch in diameter, are drilled through the tubing. Apertures 26 may be drilled by any suitable means, such as by twisting sharpened metal tubing into the silicone elastomer.

Plugs 35 are compression molded and then inserted into and bonded within open ends 42, 44 of retaining means 16, 22 with room temperature vulcanizing silicone. A mandrel is then inserted into lumen 32 and a room temperature vulcanizing silicone mixed with dye is used to silk screen markings 28 onto stent 10.

Radiopaque marker 27 is formed by cutting a silicone tube filled with tantalum into small donut pieces approximately 3 mm wide. One donut piece is placed at the base of one retaining means. Both radiopaque marker 27 and plugs 35 are sealed with room temperature vulcanizing silicone.

After radiopaque marker 27 and plugs 35 are sealed, retaining means 22, which does not have radiopaque marker 27, is cut off. Adapter means 20 is pressed tightly within lumen 32 of open end 38 of connector 14.

Stent 10 is then washed in a mild soap solution, preferably Ivory Snow, rinsed in pure water and rinsed in isopropyl alcohol. Guidewire 42 and catheter pusher 46 are also washed. Stent 10 is packaged with washed guidewire 42 and catheter pusher 46 in a thermoformed (PTEG) tray, preferably Kodar, preferably with a Tyvek lid. The tray is packaged in a standard box and sterilized using ethylene oxide gas.

The foregoing description has been directed to a particular embodiment of the invention in accordance with the requirements of the Patent Statutes for the purposes of illustration and explanation. It will be apparent, however, to those skilled in this art that many modifications and changes of the invention would be possible without departing from the scope and spirit of the invention. It is intended that the following claims be interpreted to embrace all such modifications and changes.

I claim:

1. A connector stent comprising:
   an elongated tubular member having a wall with apertures therethrough, and comprising a retaining means and an essentially straight custom trimmed portion terminating in an axial opening; and
   a connector comprising a retaining means and an adapter means that is fixedly secured within said axial opening of said straight custom trimmed portion.

2. A connector stent according to claim 1 wherein said connector has a large diameter than said elongated tubular member.

3. A connector stent according to claim 1 wherein a continuous lumen is formed when said elongated tubular member and said connector are engaged.

4. A connector stent according to claim 1 wherein said adapter means is comprised of thermoplastic.

5. A connector stent according to claim 1 wherein said elongated tubular member and said retaining means of said connector stent are composed of silicone elastomer.

6. A connector stent according to claim 5 wherein the durometer of said silicone elastomer is between 70-90 Shore A.

7. A connector stent according to claim 2 wherein said diameter of said connector is 2-3 French larger than said diameter of said elongated tubular member.

8. A connector stent according to claim 1 wherein said retaining means of said elongated tubular member has a closed end.

9. A connector stent according to claim 1 wherein said elongated tubular member is marked for measurement.

10. A method for providing drainage of a biological fluid passage through a connector stent comprising the steps of:
    measuring the length of said fluid passage;
    custom trimming an essentially straight portion of said connector stent to a length corresponding to said fluid passage length such that said straight portion terminates in an axial opening;
    fixedly securing a connector within said axial opening of said custom trimmed straight portion; and
    inserting said connector stent to a predetermined position within said fluid passage.

11. Method according to claim 10 wherein said step of inserting said connector stent comprises the steps of:
    cutting a plug off of said connector;
    inserting a guidewire through said connector stent;
    inserting said guidewire and stent into said fluid passageway; and
    removing said guidewire.

12. A method according to claim 10 wherein said step of inserting said connector stent comprises the steps of:
    inserting a guidewire into the kidney;
    cutting plugs off of both ends of said connector stent;
    inserting said connector stent onto said guidewire;
    pushing said stent into place in the kidney with a stent pusher; and
    removing said guidewire and said stent pusher.

13. Method according to claim 12 wherein said guidewire is removed by:
    inserting a catheter pusher through said fluid passageway;
    holding said connector stent in position with said catheter pusher;
    removing said guidewire; and
    removing said catheter pusher.

14. A kit for providing drainage through a biological fluid passage comprising:
    a. a guidewire;
    b. an elongated tubular member having a wall with apertures therethrough and comprising a retaining means and an essentially straight portion to be custom trimmed and terminate in an axial opening; and
    c. a connector comprising a retaining means and an adapter means for fixedly securing within said axial opening of said straight custom trimmed portion.

15. A kit according to claim 14 wherein said guidewire is coated with polytetraflouroethylene.

16. A kit according to claim 14 wherein said guidewire has a flexible tip for ease of insertion.

17. A kit according to claim 14 further comprising a catheter-pusher.

18. A kit according to claim 14 wherein said connector has a larger diameter than said elongated tubular member.

19. A kit according to claim 14 wherein a continuous lumen is formed when said elongated tubular member and said connector are engaged.

20. A kit according to claim 14 wherein said adapter means is composed of thermoplastic material.

21. A kit according to claim 14 wherein said elongated tubular member and said retaining means of said connector stent are composed of silicone elastomer.

22. A kit according to claim 21 wherein the durometer of said silicone elastomer is between 70-90 Shore A.

23. A kit according to claim 18 wherein the diameter of said connector is 2-3 French larger than the diameter of said elongated tubular member.

24. A kit according to claim 14 wherein said retaining means of said elongated tubular member has a closed end.

25. A kit according to claim 14 wherein said elongated tubular member is marked for measurement.

26. A kit for providing drainage through a biological fluid passage comprising:
 a. a guidewire; and
 b. a ureteral connector stent comprising an elongated tubular member and a connector, said elongated tubular member comprising a retaining means and a straight tube and wherein said connector comprises a retaining means and an adapter means.

27. A ureteral stent for customized use in the ureter comprising an elongated tubular member with apertures therethrough having an essentially straight custom trimmed portion terminating in an axial opening at one end and a curved body retaining portion at the other end thereof, a shortened tubular member with apertures therethrough having a connector adapter means at one end and a curved body retaining portion at the other end thereof, said connector adapter means being fixedly secured within said axial opening of said straight trimmed portion to form the customized stent after said straight portion has been trimmed to the desired length.

28. A kit for providing drainage through a biological fluid passage comprising:
 (a) a guide wire; and
 (b) a ureteral connector stent comprising an elongated tubular member having a retaining means, a connector having a retaining means, and means for adjusting the length of said stent to accommodate various anatomies without deforming said retaining means.

29. A kit according to claim 28 wherein said connector has a larger diameter than said elongated tubular member.

* * * * *